(12) United States Patent
La Mantia et al.

(10) Patent No.: US 12,221,309 B2
(45) Date of Patent: Feb. 11, 2025

(54) METHOD AND APPARATUS FOR SPLICING THREE-LAYER TAPES

(71) Applicant: Fameccanica.Data S.p.A., San Giovanni Teatino (IT)

(72) Inventors: Vincenzo La Mantia, San Giovanni Teatino (IT); Maurizio Spiriticchio, San Giovanni Teatino (IT); Giambattista Simone, San Giovanni Teatino (IT); Gabriele Sablone, San Giovanni Teatino (IT)

(73) Assignee: Fameccanica.Data S.p.A., San Giovanni Teatino Chieti (IT)

( * ) Notice: Subject to any disclaimer, the term of this patent is extended or adjusted under 35 U.S.C. 154(b) by 177 days.

(21) Appl. No.: 17/900,913

(22) Filed: Sep. 1, 2022

(65) Prior Publication Data

US 2023/0076785 A1    Mar. 9, 2023

(30) Foreign Application Priority Data

Sep. 3, 2021 (EP) .................................. 21194754

(51) Int. Cl.
*B32B 41/00* (2006.01)
*A61F 13/02* (2006.01)
*B65H 19/18* (2006.01)
*A61F 13/00* (2006.01)

(52) U.S. Cl.
CPC ......... *B65H 19/18* (2013.01); *A61F 13/0283* (2013.01); *A61F 13/0289* (2013.01); *A61F 2013/00604* (2013.01); *B65H 2301/46078* (2013.01); *B65H 2301/4631* (2013.01); *B65H 2301/515323* (2013.01); *B65H 2701/1924* (2013.01)

(58) Field of Classification Search
CPC .......... B65H 19/18; B65H 2301/46078; B65H 2301/4631; B65H 2301/515323; B65H 2701/1924; B65H 19/1831; B65H 19/1873; B65H 2301/51122; B65H 2301/5151; B65H 2406/33; A61F 13/0283; A61F 13/0289; A61F 2013/00604; A61F 13/0276
USPC ... 156/60, 64, 134, 157, 350, 351, 378, 379, 156/502, 504, 545
See application file for complete search history.

(56) References Cited

U.S. PATENT DOCUMENTS

| 3,967,994 | A | 7/1976 | Langberg |
| 4,904,875 | A | 2/1990 | Shankel |
| 2010/0215884 | A1* | 8/2010 | Kitada ................ B29C 65/5021 156/60 |

FOREIGN PATENT DOCUMENTS

JP   2002096952 A   4/2002

OTHER PUBLICATIONS

European Search Report dated Mar. 8, 2022. 6 pages.

* cited by examiner

*Primary Examiner* — Michael N Orlando
*Assistant Examiner* — Joshel Rivera
(74) *Attorney, Agent, or Firm* — RMCK Law Group PLC

(57) ABSTRACT

A method and apparatus for automatically splicing two continuous three-layer tapes, wherein a longitudinally movable continuous wound tape is transversely cut so as to form individual wound pads which are applied in longitudinally spaced positions on adhesive surfaces of continuous carrier foils, and wherein a splicing element is cut from the continuous wound tape and is applied on tail and head portions of two continuous carrier foils.

13 Claims, 3 Drawing Sheets

METHOD AND APPARATUS FOR SPLICING THREE-LAYER TAPES

CROSS-REFERENCE TO RELATED APPLICATION

This application claims priority to European Patent Application No. 21194754.4 filed Sep. 3, 2021. The disclosure of the above application is incorporated herein by reference in its entirety.

FIELD OF THE INVENTION

The present invention relates in general to manufacturing sanitary products.

The invention was developed, in particular, in view of the application in the field of manufacturing plasters, such as, for example, plasters for covering wounds, medicated plasters, pain-relieving plasters, heating plasters with and without medicaments.

More precisely, the invention relates to a method and apparatus for splicing three-layer tapes, in particular in a machine for manufacturing plasters.

In the following description, reference will be made to this specific field without however losing generality.

DESCRIPTION OF THE PRIOR ART

A plaster typically includes a carrier foil having an adhesive surface and a wound pad attached to the adhesive surface of the carrier foil. The wound pad is adapted to be placed directly over a wound and held on the skin by the adhesive carrier foil.

The carrier foil may be transparent or skin—colored and has a layer of pressure sensitive, medical grade, hypoallergenic adhesive on an entire surface. The wound pad is adhered to the adhesive layer of the carrier foil. The wound pad is made of one or more layers of gauze or other suitable material having the capacity of absorbing small quantities of exudate from a wound. The wound pad may contain medications, e.g., disinfectant, or coagulant medications. A plaster usually includes removable protective sheets applied over the wound pad and the portion of the adhesive surface of the carrier foil surrounding the wound pad. These removable protective sheets will be peeled free from the adhesive surface of the carrier foil at the time of application of the plaster to a wound. In many cases, the plasters are packaged individually in envelope-shaped packages.

Plasters are usually manufactured starting from a continuous three-layer tape, including a continuous carrier foil having an adhesive surface and first and second protective films applied, respectively, on the adhesive surface of the continuous carrier foil and on the surface of the carrier foil opposite the adhesive surface.

The continuous three-layer tape is unwound from a reel and is advanced in a longitudinal direction. The first protecting film is removed to expose the adhesive surface of the continuous carrier foil and discrete wound pads longitudinally spaced from each other are adhered on the adhesive surface of the continuous carrier foil. The second protecting film is removed before or after adhering the wound pads on the continuous carrier foil. Then, a continuous protective sheet is applied on the adhesive surface of the continuous carrier foil over the array of discrete wound pads. Finally, the composite tape thus formed is transversely cut to form individual plasters, which may be enclosed in individual envelopes formed by two flexible sheets overlapping each other that are joined together at their edges by adhesive.

When a reel containing a first continuous three-layer tape is about to be finished, the tail portion of the first continuous three-layer tape must be spliced to the head portion of a second continuous three-layer tape contained in a new reel.

Splicing of two continuous webs is usually made by applying an adhesive splicing element across the tail and head portions of the two continuous webs.

In the prior art there are various automatic splicers which are able to automatically splice the tail and head portions of two continuous webs without interrupting the supply of the continuous web.

When the tapes to be spliced include two outer layers which cover a central layer, the existing splicers are only able to apply adhesive splicing elements on the two outer layers. Existing splicers are not able to automatically apply splicing elements on not-exposed central layers of three-layer tapes.

For this reason, in the prior art machines for manufacturing plasters which use continuous three-layer tapes, splicing the three-layer tapes at the time of changing reels is carried out manually. Usually, the machine for manufacturing plasters must be stopped for allowing the manual splicing.

OBJECT AND SUMMARY OF THE INVENTION

The object of the present invention is to provide a method and apparatus for splicing three-layer tapes which overcome the problems of the prior art.

More specifically, an object of the present invention is to provide a method and apparatus which carry out automatic splicing of three-layer tapes without stopping the manufacturing machine.

According to the present invention, this object is achieved by a method and apparatus having the features of claims 1 and 7.

Optional features of the invention form the subject of the dependent claims.

The claims are an integral part of the disclosure submitted in relation to the invention.

BRIEF DESCRIPTION OF THE DRAWINGS

The present invention will now be described in detail with reference to the attached drawings, given purely by way of non-limiting example, wherein.

Figure 1:
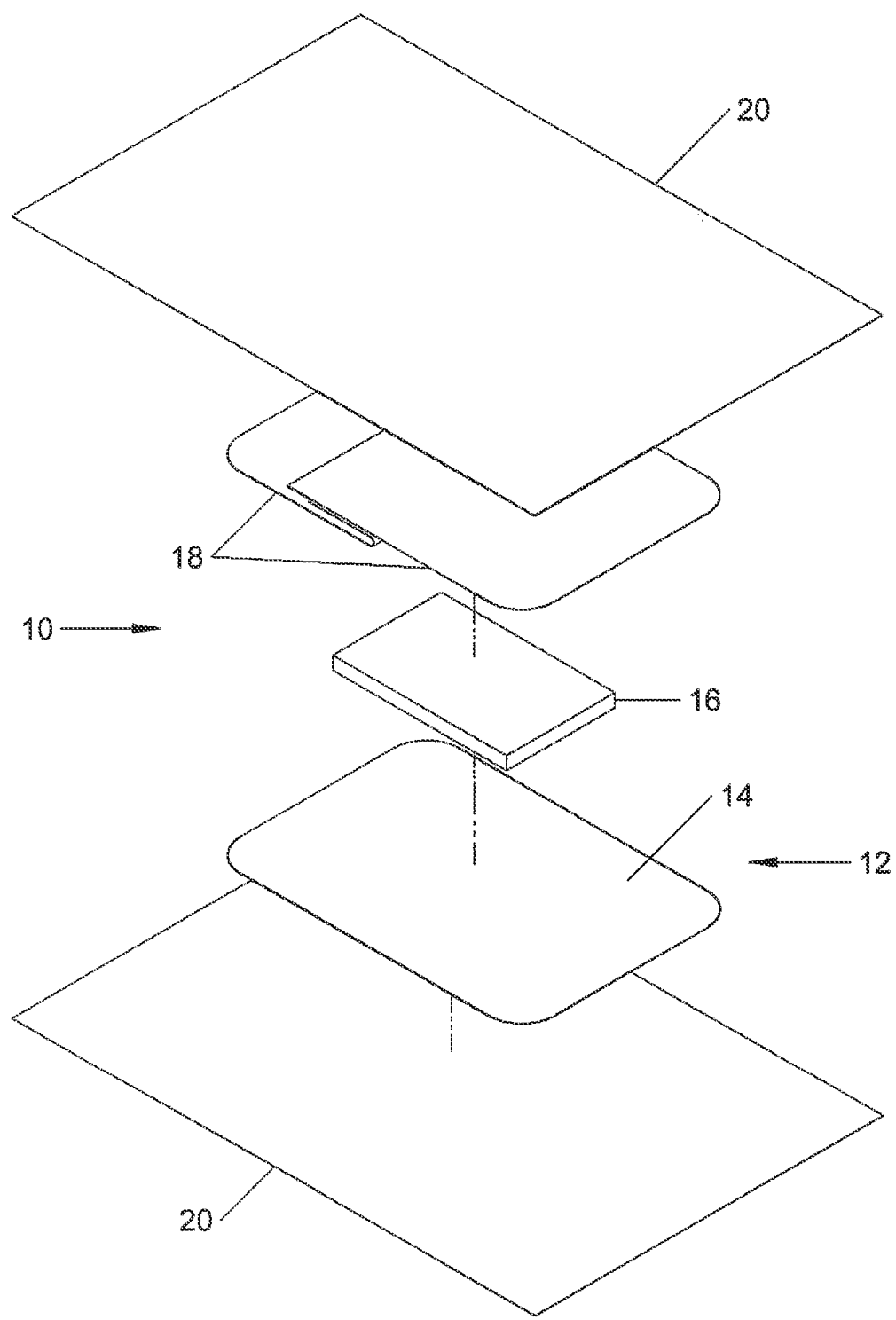
FIG. 1 is an exploded perspective view of a plaster.

It will be appreciated that in the drawings some components may not be illustrated to simplify the understanding of the figures, and that various figures may not be represented on the same scale.

DETAILED DESCRIPTION

With reference to FIG. 1, a plaster 10 includes a carrier foil 12 having an adhesive surface 14, and a wound pad 16 attached to the adhesive surface 14 of the carrier foil 12. The wound pad 16 is adapted to be placed directly over a wound and held on the skin by the adhesive carrier foil 12.

The carrier foil 12 may be formed by a transparent or skin—colored plastic film. The adhesive surface 14 of the carrier foil 12 may be formed by a layer of pressure sensitive, medical grade, hypoallergenic adhesive applied on the entire surface of the carrier foil 12.

The wound pad 16 is adhered to the adhesive surface 14 of the carrier foil 12. The wound pad 16 is made of one or more layers of gauze or other suitable material having the capacity of absorbing small quantities of exudate from a wound. The wound pad 16 may contain medications, e.g., disinfectant, or coagulant medications.

The plaster 10 may include a pair of removable protective sheets 18 applied over the wound pad 16 and the portion of the adhesive surface 14 of the carrier foil 12 which surrounds the wound pad 16. The removable protective sheets 18 will be peeled free from the adhesive surface 14 of the carrier foil 12 at the time of application of the plaster 10 to a wound.

The plaster 10 may be packaged individually between two packaging sheets 20 which are joined to each other around the plaster 10, e.g., by pressure sensitive adhesive, to form an envelope-shaped package.

Figure 2:
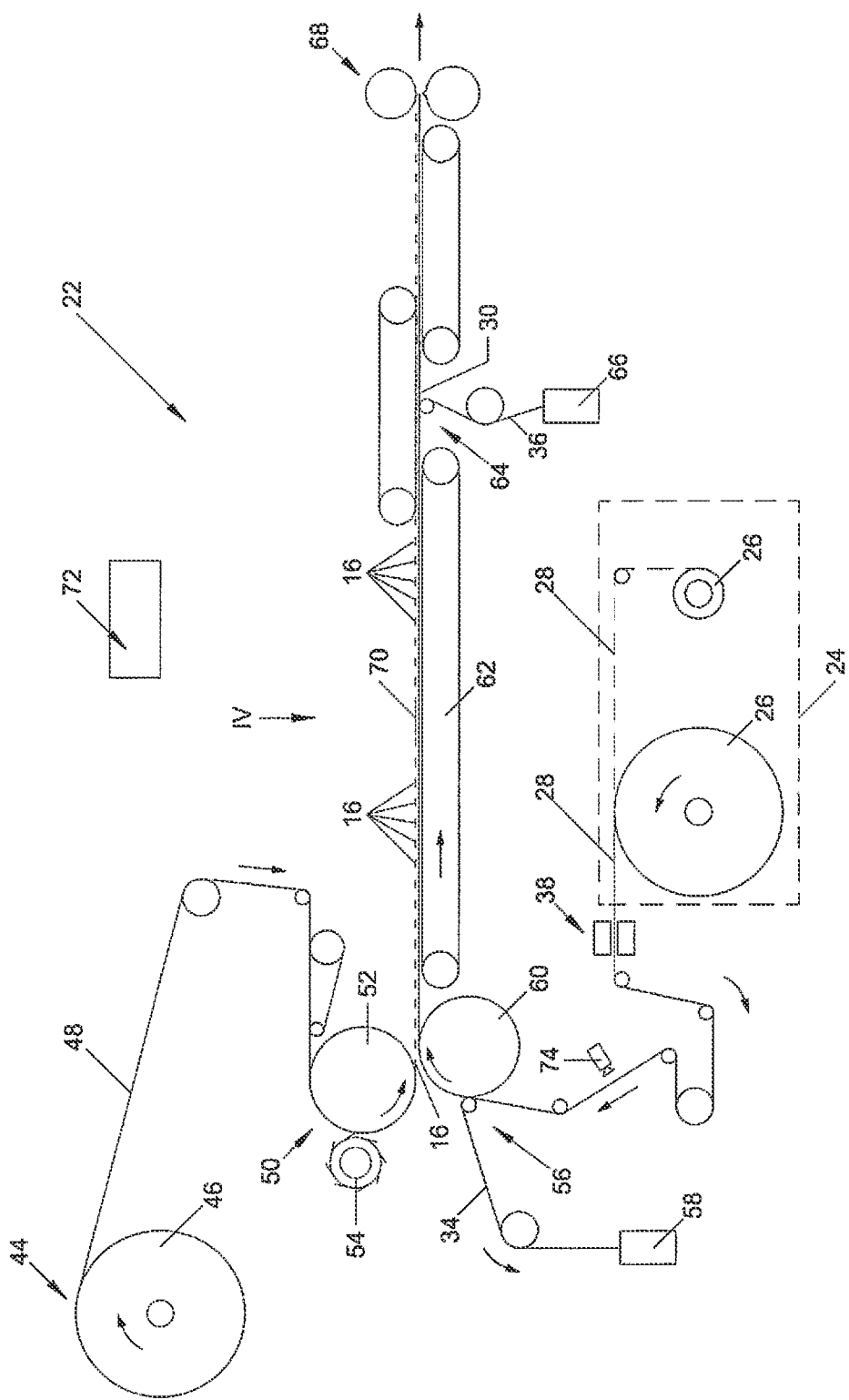
FIG. 2 is a schematic side view of an apparatus for manufacturing the plaster of FIG. 1.

With reference to FIG. 2, an apparatus for manufacturing plasters 10 of the type previously disclosed is schematically indicated by numeral reference 22.

The apparatus 22 comprises an unwinding unit 24 configured for unwinding continuous three-layer tapes 28 from respective reels 26. While one of the reels 26 supplies a first continuous three-layer tape 28, the other reel 26 is kept in reserve in an inoperative position. When the first reel is exhausted, the tail portion of the first continuous three-layer tape 28 coming from an exhausted reel 26 is spliced to a head portion of the second continuous three-layer tape 28 unwound from the replacement reel 26, as it will be disclosed in the following.

Figure 3:
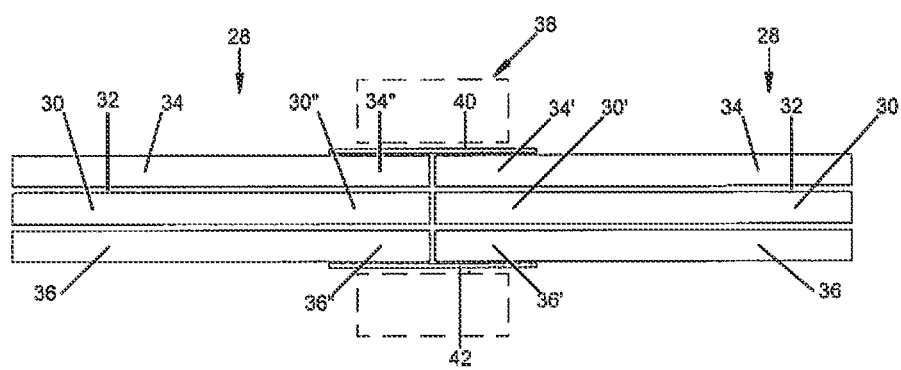
FIG. 3 is an enlarged schematic cross section of a splicing region between two three-layer tapes before the removal of the protecting films.

With reference to FIG. 3, each continuous three-layer tape 28 includes a continuous carrier foil 30 having an adhesive surface 32, a continuous top protective film 34 applied on the adhesive surface 32 of the continuous carrier foil 30 and a continuous back protective film 36 applied on the surface of the continuous carrier foil 30 opposite the adhesive surface 32.

With reference to FIG. 2, the apparatus 22 comprises a splicing unit 38 which is configured for splicing a tail portion of a first continuous three-layer tape 28 coming from an exhausted reel 26 to a head portion of a second continuous three-layer tape 28 coming from a replacement reel 26.

With reference to FIGS. 2 and 3, the splicing unit 38 is configured for applying a top adhesive splicing element 40 across tail and head portions 34', 34" of the two continuous top protective films 34 and a back adhesive splicing element 42 on tail and back portions 36', 36" of the two continuous back protective films 36. Tail and head portions 30', 30" of the two continuous carrier foils 30 remain not spliced.

The application of the top and back adhesive splicing elements 40, 42 may be carried out with standard automatic splicers which are well known in the state of the art, for instance in machines for manufacturing absorbent sanitary products.

With reference to FIG. 2, the apparatus 22 comprises a second unwinding unit 44 configured for unwinding from a reel 46 a continuous wound tape 48. After being unwound from the respective reel 46 the continuous wound tape 48 is advanced longitudinally.

The apparatus 22 comprises a cut-and-slip unit 50 configured for transversely cutting the continuous wound tape 48 to form individual wound pads 16 spaced apart from each other in the longitudinal direction. The cut-and-slip unit 50 comprises a rotating anvil roller 52 and a rotating knife 54 cooperating with the outer surface of the rotating anvil roller 52 to cut the continuous wound tape 48 transversely to the longitudinal direction. After the transversal cut of the continuous wound tape 48, the individual wound pads 16 are retained, e.g., by suction, on the outer surface of the rotating anvil roller 52.

The apparatus 22 comprises a first delamination unit 56 configured for removing the top protective film 34 from the continuous carrier foil 30, to expose the adhesive surface 32 of the continuous carrier foil 30. The continuous top protective film 34 removed from the continuous carrier foil 30 is disposed as scrap, for instance in a first shredder 58.

The first delamination unit 56 comprises an application roller 60 having an outer surface facing the outer surface of the rotating anvil roller 52. The continuous carrier foil 30 passes on the outer surface of the application roller 60 with the adhesive surface 32 facing the rotating anvil roller 52. On the application roller 60 the individual wound pads 16 are pressed and fixed on the adhesive surface 32 of the continuous carrier foil 30 in longitudinally spaced positions.

Downstream of the application roller 60 the continuous carrier foil 30 with the wound pads 16 applied thereon is transported on a conveyor 62 to a second delamination unit 64, where the back protective film 36 is delaminated from the continuous carrier foil 30. The continuous back protective film 36 removed from the continuous carrier foil 30 is disposed as scrap, for instance in a second shredder 66.

Then, the continuous carrier foil 30 is cut transversely in a cutting unit 68 to form individual plasters 10. Before transversally cutting the continuous carrier foil 30, removable protective sheets (not shown) may be applied on the on the adhesive surface 32 of the continuous carrier foil 30.

In operation, the continuous three-layer tape 28 unwound from the respective reel 46 is advanced longitudinally toward the first delamination unit 56. In the first delamination unit 56 the top protective film 34 is removed from the continuous carrier foil 30, to expose the adhesive surface 32 of the continuous carrier foil 30.

In the cut-and-slip unit 50 the continuous wound tape 48 is cut transversely to form individual wound pads 16 longitudinally spaced from each other, which are adhered to the adhesive surface 32 of the continuous carrier foil 30. During the normal production of plasters 10, the cut-and-slip unit 50 cuts wound pads 16 having all the same dimension in the longitudinal direction and spaced apart from each other by a constant distance.

When the reel 26 which supplies the first three-layer tape 28 is exhausted, the splicing unit splices automatically the tail portion of the first continuous three-layer tape 28 coming from the exhausted reel 26 to the head portion of the second continuous three-layer tape 28 coming from the replacement reel 26.

At the first delamination unit 56, the tail and head portions of the two continuous top protective films 34 are spliced to each other, so that delamination of the top protective film 34 continues without interruptions.

Immediately after the removal of the two continuous top protective films 34, the tail and head portions of the two continuous carrier foils 30 are not spliced to each other.

Figure 4:
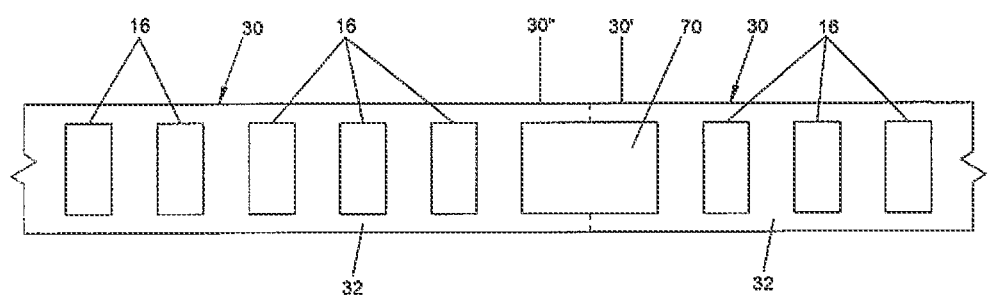
FIG. 4 is a plan view of the splicing region between two three-layer tapes taken along the line IV in FIG. 2.

With reference to FIG. 4, during the splicing operation, the cut-and-slip unit 50 is configured for cutting from the continuous wound tape 48 a splicing element 70 and for applying the splicing element 70 on the adhesive surfaces 32 on tail and head portions 30', 30" of the two continuous carrier foils 30.

The splicing element 70 is made of the same material as the wound pads 16 and is applied on the adhesive surfaces 32 of the two continuous carrier foils 30 on the application roller 60 in the same way as the wound pads 16. However, differently from the wound pads 16, the splicing element 70 is applied across the tail and head transverse edges of the two continuous carrier foils 30, so that the two continuous carrier foils 30 are spliced to each other by an element made of the same material as that forming the wound pads 16.

Therefore, the same cut-and-slip unit which forms and applies the wound pads 16 on the continuous carrier foil 30 during the ordinary production of plasters is used for automatically splicing tail and head portions 30', 30" of two continuous carrier foils 30 at the time of a change of reels 26.

A considerable advantage of this solution is that there is no need for a separate splicing unit for splicing the two continuous carrier foils 30, which reduces the cost and the dimensions of the apparatus 22.

In a possible embodiment, the cut-and-slip unit 50 is configured for cutting from the wound tape 48 a splicing element 70 having an extension in the longitudinal direction which is greater than the extension in the longitudinal direction of the wound pads 16.

The splicing element 70 may have an extension in the longitudinal direction which is comprised between 3-6 times the extension in the longitudinal direction of the wound pads 16. This increases the strength of the splicing region. The plasters 10 adjacent to the splicing region are disposed as wastes as customary in the field.

The apparatus 22 comprises a motion control system 72 which controls the operation of all the motor driven elements of the apparatus 22. The motion control system 72 may be a programmable computer in which a computer program is installed, the computer program being configured for implementing a method for automatically splicing three-layer tapes 28 in a machine for manufacturing plasters.

In a possible embodiment the apparatus 22 may comprise a sensor 74 arranged for detecting the position of one of the top or back adhesive splicing elements 40, 42 on the longitudinally movable first and second continuous three-layer tapes 28. The detection signal generated by the sensor 74 may be sent to the motion control system 72 which controls the cut-and-slip unit 50 to cut and apply the splicing element 70 on the continuous carrier foils 28 in phase with the splicing region defined by the position of the top or back adhesive splicing elements 40, 42.

In a possible embodiment, the speed of the rotating anvil roller 52 remains constant while the speed of the rotating knife 54 of the cut-and-slip unit 50 is selectively variable between a first speed when cutting the wound pads 16 and a second speed lower than the first speed when cutting the splicing element 70.

After the application of the splicing element 70 the speed of the rotating knife 54 returns to the first speed at which the wound pads 16 are cut.

Of course, without prejudice to the principle of the invention, the details of construction and the embodiments can be widely varied with respect to those described and illustrated, without thereby departing from the scope of the invention as defined by the claims that follow.

The invention claimed is:

1. A method for manufacturing plasters including automatically splicing two continuous three-layer tapes, the method comprising:
   providing two longitudinally movable continuous three-layer tapes, each including a continuous carrier foil having an adhesive surface, a top protective film applied on the adhesive surface of the continuous carrier foil and a back protective film applied on a surface of the carrier foil opposite the adhesive surface,
   applying a top adhesive splicing element on tail and head portions of the top protective films and a back adhesive splicing element on tail and head portions of the back protective films,
   delaminating the top protective films to expose the adhesive surfaces of the two continuous carrier foils,
   providing a longitudinally movable continuous plaster wound tape, transversely cutting said continuous plaster wound tape to form individual wound pads and applying said wound pads in longitudinally spaced positions on the adhesive surfaces of the continuous carrier foils, and
   cutting from said continuous plaster wound tape a plaster splicing element and applying said plaster splicing element on the adhesive surfaces of the two continuous carrier foils on tail and head portions of the continuous carrier foils.

2. The method of claim 1, wherein said splicing element has an extension in a longitudinal direction which is greater than an extension in the longitudinal direction of said wound pads.

3. The method of claim 1, wherein the extension in the longitudinal direction of said splicing element is comprised between 3-6 times the extension in the longitudinal direction of said wound pads.

4. The method of claim 1, wherein said continuous wound tape is cut in a cut-and-slip unit including a rotating knife cooperating with a rotating anvil roller, and wherein said splicing element is formed by slowing down the rotating knife with respect to a speed at which the rotating knife cuts said wound pads.

5. The method of claim 4, comprising detecting a position of one of said top or back adhesive splicing elements on the longitudinally movable continuous three-layer tapes and controlling said rotating knife so as to cut and apply said splicing element on the tail and head portions of the continuous carrier foils in phase with the detected position of said top or back adhesive splicing elements.

6. The method of claim 1, comprising delaminating the back protective films after applying said splicing element on the tail and head portions of the continuous carrier foils.

7. An apparatus for manufacturing plasters including automatically splicing two continuous three-layer tapes, the apparatus comprising:
   an unwinding unit configured for unwinding from respective reels two longitudinally moving three-layer tapes, each including a continuous carrier foil having an adhesive surface, a top protective film applied on the adhesive surface of the continuous carrier foil and a back protective film applied on a surface of the continuous carrier foil opposite the adhesive surface,
   a splicing unit configured for applying a top adhesive splicing element on tail and head portions of the top protective films and a back adhesive splicing element on tail and head portions of the back protective films,
   a first delamination unit configured for removing the top protective films to expose the adhesive surfaces of the continuous carrier foils,
   a second unwinding unit configured for unwinding from a reel a longitudinally moving continuous plaster wound tape,
   a cut-and-slip unit configured for transversely cutting said continuous plaster wound tape to form individual plaster wound pads and for applying said plaster wound pads in longitudinally spaced positions on the adhesive surfaces of the continuous carrier foils, wherein said cut-and-slip unit is also configured for cutting from said continuous plaster wound tape a plaster splicing element and for applying said plaster splicing element on the adhesive surfaces of the two continuous carrier foils on tail and head portions of the continuous carrier foils.

8. The apparatus of claim 7, wherein said cut-and-slip unit is configured for cutting a splicing element having an extension in a longitudinal direction which is greater than an extension in the longitudinal direction of the wound pads.

9. The apparatus of claim 8, wherein said cut-and-slip unit is configured for cutting a splicing element having an extension in the longitudinal direction which is comprised between 3-6 times the extension in the longitudinal direction of said wound pads.

10. The apparatus of claim 7, wherein the cut-and-slip unit includes a rotating knife cooperating with a rotating anvil roller, and wherein a speed of the rotating knife is selectively variable between a first speed when cutting said wound pads and a second speed lower than said first speed when cutting said splicing element.

11. The apparatus of claim 10, comprising a sensor arranged for detecting a position of one of said top or back adhesive splicing elements on the longitudinally movable continuous three-layer tapes, and a motion control system configured for controlling said cut-and-slip unit so as to cut and apply said splicing element on the continuous carrier foils in phase with the detected position of said top or back adhesive splicing elements.

12. The apparatus of claim 7, comprising a second delamination unit configured for removing said back protective films from said continuous carrier foils downstream of said cut-and-slip unit.

13. A computer program installable on a motion controller, configured for implementing a method for automatically splicing three-layer tapes according to claim 1.

* * * * *

UNITED STATES PATENT AND TRADEMARK OFFICE
CERTIFICATE OF CORRECTION

PATENT NO. : 12,221,309 B2
APPLICATION NO. : 17/900913
DATED : February 11, 2025
INVENTOR(S) : Vincenzo La Mantia et al.

It is certified that error appears in the above-identified patent and that said Letters Patent is hereby corrected as shown below:

On the Title Page

Item (71) Applicant address information should be listed as:
- Fameccanica.Data S.p.A., San Giovanni Teatino (Chieti), ITALY -

Item (72) Inventor address information should be listed as:
- Vincenzo LA MANTIA, San Giovanni Teatino (Chieti), ITALY
Maurizio SPIRITICCHIO, San Giovanni Teatino (Chieti), ITALY
Giambattista SIMONE, San Giovanni Teatino (Chieti), ITALY
Gabriele SABLONE, San Giovanni Teatino (Chieti), ITALY -

Signed and Sealed this
Eighth Day of April, 2025

Coke Morgan Stewart
*Acting Director of the United States Patent and Trademark Office*